United States Patent [19]

Flury et al.

[11] Patent Number: 4,855,367

[45] Date of Patent: Aug. 8, 1989

[54] ORTHOCARBONATES

[75] Inventors: Peter Flury, Himmelried; Sameer H. Eldin, Fribourg; Martin Roth, Giffers, all of Switzerland; Claus W. Rabener, Oetlingen, Fed. Rep. of Germany

[73] Assignee: Giba-Geigy Corporation, Hawthorne, N.Y.

[21] Appl. No.: 203,792

[22] Filed: Jun. 7, 1988

[30] Foreign Application Priority Data

Jun. 10, 1987 [CH] Switzerland .......................... 2173/87

[51] Int. Cl.$^4$ ..................... C08G 59/40; C07D 493/10
[52] U.S. Cl. ........................................ 525/507; 528/96; 528/104; 528/110; 528/116; 549/334
[58] Field of Search ................. 528/110, 116, 104, 96; 525/507; 549/334

[56] References Cited

U.S. PATENT DOCUMENTS

| | | | |
|---|---|---|---|
| 3,773,790 | 11/1973 | Yoshimura et al. | 528/104 X |
| 3,845,046 | 10/1974 | Fauran et al. | 549/334 X |
| 4,183,862 | 1/1980 | Steiner | 549/334 |
| 4,368,314 | 1/1983 | Endo et al. | 528/104 X |
| 4,387,215 | 6/1983 | Bailey | 528/354 |

OTHER PUBLICATIONS

ACS Polymeric Materials Science and Engineering, vol. 54, p. 23.

*Primary Examiner*—Earl Nielsen
*Attorney, Agent, or Firm*—S. V. O'Brien

[57] ABSTRACT

Orthocarbonates of the formula I

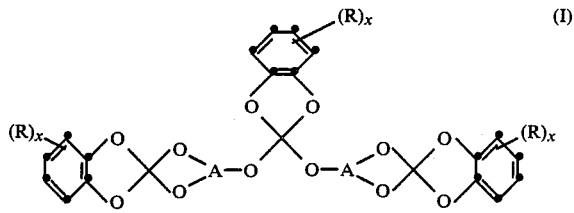

in which R is $C_1$-$C_4$alkyl, x is zero, 1 or 2, and A is a trivalent radical derived from an aliphatic triol by omitting the hydroxyl groups, the hydroxyl groups of the triol being bonded to different carbon atoms, are suitable as cocomponents in the curing of epoxy resins in that they limit the reduction in volume occurring during curing of epoxy resins. In addition, the cured resins are distinguished by increased flexural strength and impact strength.

12 Claims, No Drawings

ORTHOCARBONATES

The invention relates to novel polycyclic orthocarbonates, a process for their preparation, and their use as cocomponents in curable epoxy resin mixtures.

On curing of epoxy resins, a reduction in volume generally occurs which results in internal stresses and problems in shaping. In practice, attempts are often made to limit this decrease in volume as far as possible by adding various additives, inter alia bicyclic orthocarbonates.

Thus, U.S. Pat. No. 4,387,215 describes a process for the preparation of polymers without a decrease in volume by using spiroorthocarbonates, spiroorthoesters or polycyclic ketal lactones. Although it is stated that the spiro or polycyclic compounds used can also be employed together with other monomers in the preparation of copolymers with a reduced decrease in volume, specific copolymers of this type are not, however, disclosed.

In ACS Polymeric Materials Science and Engineering, volume 54, page 23, W. J. Bailey and coworkers describe the curing of a bisphenol-A diglycidyl ether in the presence of a bisnorbornenyl spiroorthocarbonate and the preparation of other bisaliphatic or bisaromatic spiroorthocarbonates.

However, the known orthocarbonates are not satisfactory in all respects when used as cocomponents in the curing of epoxy resins. Many of these compounds are either not sufficiently miscible with customary epoxy resins or impair the other properties of the cured products, for example the heat distortion resistance or the flexural strength. The compounds according to the invention do not have the disadvantages mentioned.

The present invention relates to orthocarbonates of the formula I

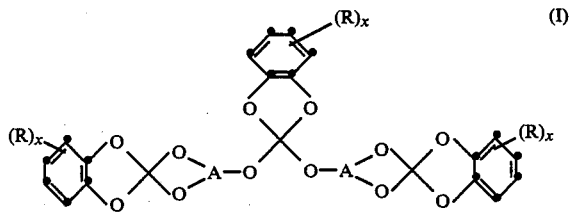

in which R is $C_1$–$C_4$alkyl, x is zero, 1 or 2, and A is a trivalent radical derived from an aliphatic triol through omission of the hydroxyl groups, the hydroxyl groups of the triol being bonded to different carbon atoms.

The orthocarbonates according to the invention can be prepared by reacting three moles of a 2,2-dichloro-1,3-benzodioxole of the formula

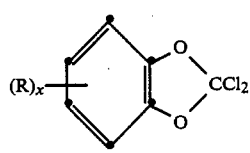

with two moles of a triol of the formula $A(OH)_3$ in the presence of a base, the symbols R, x and A being as defined above.

Preferred orthocarbonates of the formula I are those in which x is 1 and in particular zero.

Preferred compounds of the formula I are also those in which A is derived from a 1,2,-triol where n is an integer from 3 to 10, or from a 1,3,5-triol. Suitable 1,2,n-triols from which the radical A can be derived are in particular, 1,2,3-, 1,2,4- and 1,2,5-triols.

Particularly preferred compounds of the formula I are those in which A is derived from a 1,2,3-, 1,2,4- or a 1,3,5-triol, and also those in which A is a radical containing 3 to 24, in particular 3 to 12, carbon atoms.

If A is a trivalent radical derived from a 1,2,3-triol, it is preferably a radical of the formula II

where the substituents $R^1$, independently of one another, are a $C_1$–$C_4$alkyl group or, preferably, hydrogen.

If the groups R or $R^1$ are $C_1$–$C_4$alkyl groups, the latter may be straight-chain or branched, for example methyl, ethyl, n- and i-propyl, and n-, i-, sec- and tert-butyl.

Suitable 1,2,3-triols from which the radical A may be derived are, for example, the following: glycerol, 1,2,3-butanetriol, 1,2,3-pentanetriol, 2,3,4-pentanetriol, 3-methyl-1,2,3-butanetriol, 1,2,3-hexanetriol, 2,3,4-hexanetriol and 2,4-dimethyl-2,3,4-pentanetriol.

The most preferred 1,2,3-triol is glycerol.

Suitable 1,2,4- or 1,2,5-triols from which the radical A may be derived are, for example, the following: 1,2,4-butanetriol, 1,2,4-pentanetriol, 1,2,4-hexanetriol and 1,2,5-hexanetriol. 1,2,4-Butanetriol is particularly preferred here.

Suitable 1,3,5-triols from which the radical A may be derived are, for example, the following compounds: 1,1,1-trimethylolpropane[2,2-bis(hydroxymethyl)-butanol], trimethylolmethane and 1,1,1-trimethylolethane.

1,1,1-Trimethylolpropane and 1,1,1-trimethylolethane are preferred.

Preferred orthocarbonates of the formula I according to the invention are thus also those in which A is a radical of the formula III, IIIa or IIIb

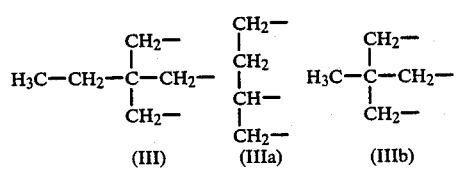

The most preferred orthocarbonates according to the invention ae those of the formulae IV to XI

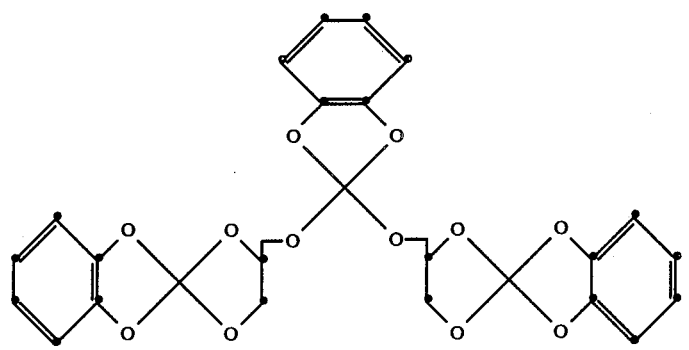
IV
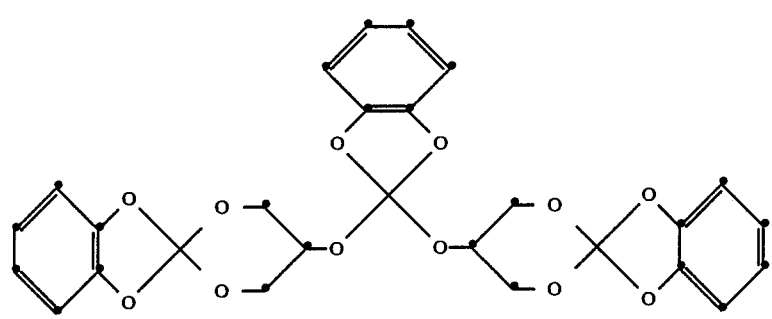
V
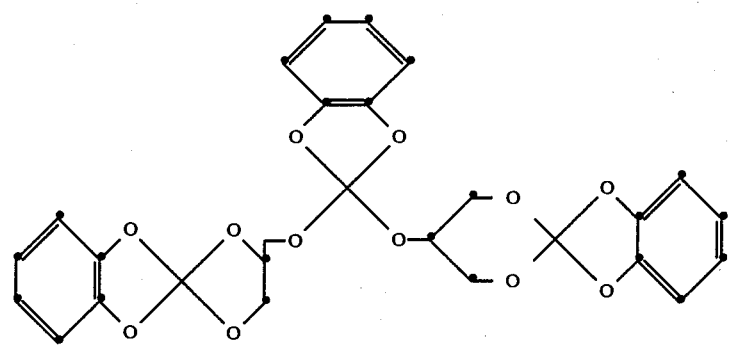
VI
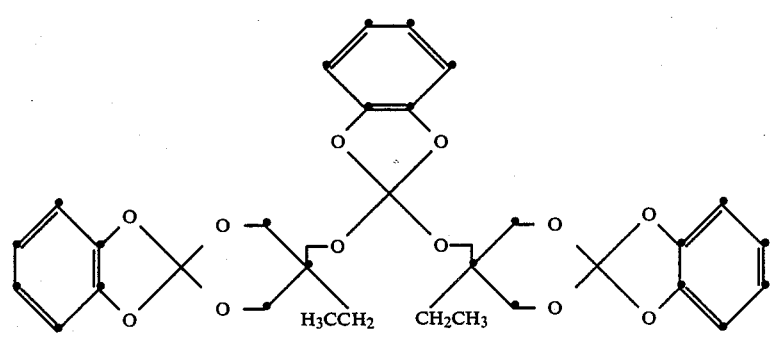
VII

-continued

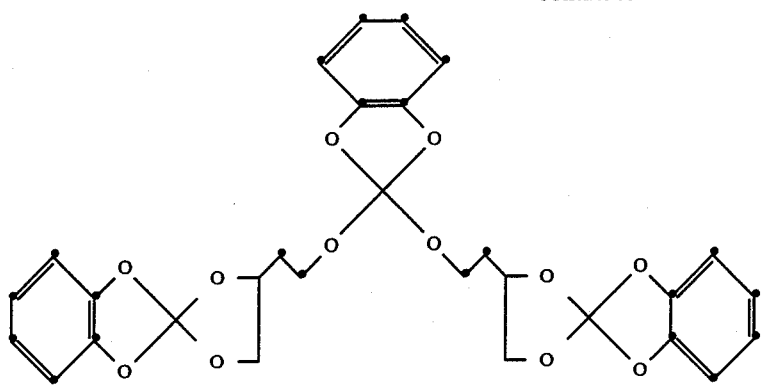

VIII

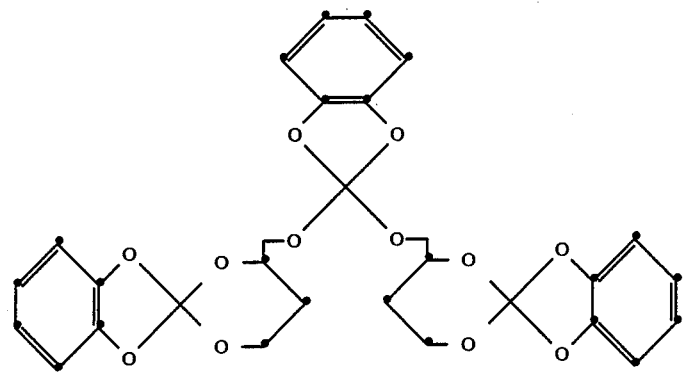

IX

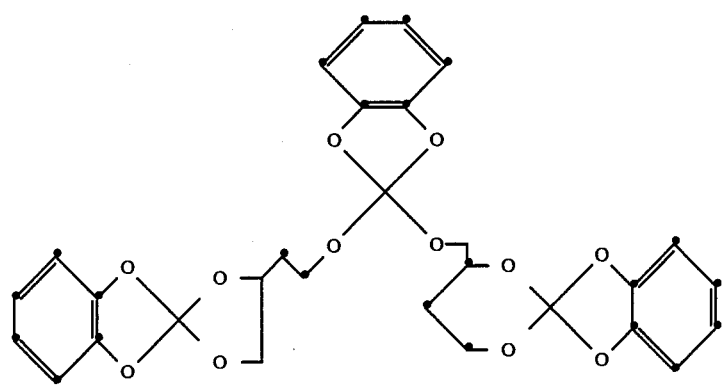

X

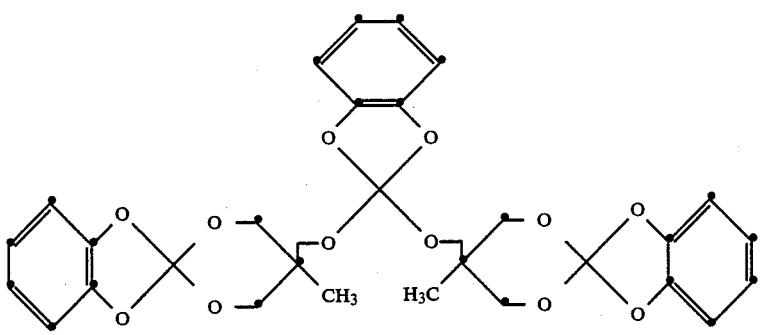

XI

These compounds are products of the reaction of 2,2-dichloro-1,3-benzodioxole with glycerol, with trimethylolpropane, with 1,2,4-butanetriol or with trimethylolethane. In the reaction with glycerol, the compound of the formula IV is the principal product, but relatively small amounts of the isomeric compounds of the formulae V and VI may also be formed.

As stated, the orthocarbonates according to the invention can be prepared by reacting 3 moles of a substituted or unsubstituted 2,2-dichloro-1,3-benzodioxole with 2 moles of a triol in the presence of a base. Suitable bases are, in particular, tertiary amines, for example triethylamine or pyridine. The amount of base correspond at least to the amount of acid set free by the reaction. However, it is also possible to use an excess of the base, so that the latter also, in part, serves as solvent. The reaction preferably takes place in an inert solvent, for example toluene, methylene chloride, chloroform or ethyl acetate, if expedient with simultaneous cooling of the reaction mixture. The orthocarbonate product obtained in the reaction is isolated from the reaction mixture and can be further used directly, irrespective of whether relatively small amounts of isomeric by-products (for example compounds of the formulae V and VI) are produced in addition to the principal product (for example the compound of the formula IV).

The starting materials used in the reaction are known and can be prepared in a known manner. The substituted or unsubstituted 2,2-dichloro-1,3-benzodioxoles can be prepared, for example, as described in Houben-Weyl, "Methoden der organischen Chemie" [Methods of Organic Chemistry], Vol. E4, 667–668, Thieme Verlag, Stuttgart 1983, by chlorination of 1,3-benzodioxoles or 2-oxo-1,3-benzodioxoles. The triols used in the preparation of the compounds according to the invention are known and commercially available.

The orthocarbonates according to the invention are readily miscible with epoxy resins in a broad mixing ratio and react with the epoxy resin curing system during curing to produce cured products havine excellent properties.

The invention also relates to curable mixtures of substances containing
(a) an orthocarbonate of the formula I according to the invention,
(b) an epoxy resin and
(c) a curing agent and, if desired, a curing catalyst for the epoxy resin.

The curable mixtures of substances according to the invention preferably contain 5 to 50, particularly preferably 10 to 40, in particular 15 to 35, parts by weight of the orthocarbonate (a) per 100 parts by weight of the epoxy resin (b).

The orthocarbonates according to the invention reduce, in a sustained manner, the reduction in volume which usually occurs during curing of epoxy resins and which otherwise impairs the properties of the cured products. The invention therefore also relates to the use of the orthocarbonates of the formula I as cocomponents in curing of epoxy resins for reducing the reduction in volume which occurs during curing of epoxy resins.

Components (a), (b) and (c) of the mixtures according to the invention may in each case be pure substances or mixtures.

In the mixtures of substances according to the invention, all customary epoxy resins are suitable as component (b). The following may be mentioned in particular:

Alicyclic polyepoxides, such as epoxyethyl-3,4-epoxycyclohexane (vinyl cyclohexene diepoxide), limonene diepoxide, dicyclopentadiene diepoxide, bis(3,4-epoxycyclohexylmethyl)adipate, 3',4'-epoxycyclohexylmethyl 3,4-epoxycyclohexanecarboxylate, 3',4'-epoxy-6'-methylcyclohexylmethyl 3,4-epoxy-6-methylcyclohexanecarboxylate, 3-(3',4'-epoxycyclohexyl)-2,4-dioxaspiro[5,5]-8,9-epoxyundecane and 3-glycidyloxyethoxyethyl-2,4-dioxaspiro[5,5]-8,9-epoxyundecane.

Diglycidyl or polyglycidyl ethers of polyhydric alcohols, such as 1,4-butanediol, or polyalkylene glyciols, such as polypropylene glycols, diglycidyl or polyglycidyl ethers of cycloaliphatic polyols, such 2,2-bis(4-hydroxycyclohexyl)propane, diglycidyl or polyglycidyl ethers of polyhydricphenols, such as resorcinol, bis(p-hydroxyphenyl)methane (bisphenol F), 2,2-bis(p-hydroxyphenyl)propane (bisphenol A), 2,2-bis(4'-hydroxy-3',5'-dibromophenyl)propane, 1,1,2,2-tetrakis(p-hydroxyphenyl)ethane, or products, obtained under acid conditions, of the condensation of phenols with formaldehyde, such as phenol novolaks and cresol novolaks; furthermore di($\beta$-methylglycidyl) or poly($\beta$-methylglycidyl) ethers of the abovementioned polyalcohols and polyphenols.

Polyglycidyl esters and poly($\beta$-methylglycidyl) esters of polybasic carboxylic acids, such as phthalic acid, terephthalic acid, tetrahydrophthalic acid and hexahydrophthalic acid.

N-Glycidyl derivatives of amines, amides and heterocyclic nitrogen bases, such as N,N-diglycidylaniline, N,N-diglycidyltoluidine, N,N,N',N'-tetraglycidyl bis(p-aminophenyl)methane, triglycidyl isocyanurate, N,N'-diglycidylethyleneurea, N,N'-diglycidyl-5,5-dimethylhydantoin, N,N'-diglycidyl-5-isopropylhydantoin and N,N'-diglycidyl-5,5-dimethyl-6-isopropyl-5,6-dihydrouracil.

The customary curing agents for epoxy resins can be employed as component (c) in the mixtures of substances according to the invention. Examples of these are:

Aliphatic, cycloaliphatic, aromatic and heterocyclic amines, such as bis(4-aminophenyl)methane, anilineformaldehyde resins, bis(4-aminophenyl)sulfone, propane-1,3-diamine, hexamethylenediamine, diethylenetriamine, triethylenetetramine, 2,2,4-trimethylhexane-1,6-diamine, m-xylylenediamine, bis(4-aminocyclohexyl)methane, 2,2-bis(4-aminocyclohexyl)propane and 3-aminomethyl-3,5,5-trimethylcyclohexylamine(isophoronediamine), polyaminoamides, for example those prepared from aliphatic polyamines and dimerized or trimerized fatty acids, polyphenols, such as resorcinol, hydroquinone, 2,2-bis(4-hydroxyphenyl)propane and phenolaldehyde resins, polythiols, such as the polythiols commercially available under the name "Thiokols", polycarboxylic acids and anhydrides thereof, for example phthalic anhydride, tetrahydrophthalic anhydride, hexahydrophthalic anhydride, hexachloroendomethylenetetrahydrophthalic anhydride, pyromellitic dianhydride, benzophenone-3,3',4,4'-tetracarboxylic dianhydride, the acids of the abovementioned anhydrides, and also isophthalic acid and terephthalic acid. It is also possible to use catalytically active curing agents, for example tin salts of alkanoic acids (for example tin octanoate), Friedel-Crafts catalysts, such as boron trifluoride and boron trichloride, and complexes and chelates thereof which are obtained by reacting boron trifluoride with, for example, 1,3-diketones.

The amount of the curing agent employed depends on the chemical nature of the curing agent and on the desired properties of the curable mixture and the cured product. The optimum amount can easily be determined. If the curing agent is an amine, 0.75 to 1.25 equivalents of amine hydrogen are normally used per equivalent of epoxide. If polycarboxylic acids or anhydrides thereof are employed, 0.4 to 1.1 equivalents of carboxyl groups or anhydride groups are usually used per equivalent of epoxide groups. When polyphenols are used as curing agents, 0.75 to 1.25 phenolic hydroxyl groups are expediently employed per epoxide equivalent.

Catalytically active curing agents are generally employed in amounts from 1 to 40 parts by weight per 100 parts by weight of epoxy resin.

If desired, active diluents, for example styrene oxide, butyl glycidyl ether, 2,2,4-trimethylpentyl glycidyl ether, phenyl glycidyl ether, cresyl glycidyl ether or glycidyl esters of synthetic, highly branched mainly tertiary aliphatic monocarboxylic acids, may be added to the curable mixtures in order to reduce the viscosity.

It is also possible to employ curing accelerators during the curing; such accelerators are, for example, tertiary amines, the salts or quaternary ammonium compounds thereof, for example benzyldimethylamine, 2,4,6-tris(dimethylaminomethyl)phenol, 1-methylimidazole, 2-ethyl-4-methylimidazole, 4-aminopyridine and tripentylammonium phenolate; or alkali metal alkoxides, for example Na alkoxides of 2,4-dihydroxy-3-hydroxymethylpentane. The mixtures according to the invention are expediently cured in the temperature range 50° C. to 300° C., preferably 80°–250° C.

The curing can also be carried out in a known fashion in two or more steps, the first curing step being carried out at low temperature and the post-curing at elevated temperature.

If desired, the curing can also be carried out in 2 steps in a manner such that the curing reaction is initially terminated prematurely or the first step is carried out at slightly elevated temperature, a curable precondensate (so-called "B stage") which is still meltable and/or soluble being obtained from the epoxy component (a) and the curing agent (b). A precondensate of this type can be used, for example, for the preparation of "prepregs", compression moulding compositions or sinter powders.

The term "cure" as used here means the conversion of soluble, either liquid or meltable polyepoxides into solid, insoluble and nonmeltable, three-dimensionally crosslinked products or materials, generally with simultaneous shaping to form mouldings, such as castings, compression mouldings and laminates, to form impregnations, coatings, surface-coating films or bondings.

The curable mixtures according to the invention may furthermore contain suitable plasticizers, such as dibutyl phthalate, dioctyl phthalate or tricresyl phthalate.

Finally, the curable mixtures according to the invention may be treated, before curing, in any phase with extenders, fillers and reinforcing agents, for example coal tar, bitumen, textile fibres, glass fibres, asbestos fibres, boron fibres, carbon fibres, mineral silicates, mica, quartz sand, aluminium oxide hydrate, bentonites, kaolin, silica aerogel or metal powders, for example aluminium powder or iron powder, furthermore with pigments and dyes, such as carbon black, oxide dyes, titanium dioxide inter alia. Furthermore, it is also possible to add other customary additives, for example flame retardants, such as antimony trioxide, trioxtropic agents, flow control agents, such as silicones, waxes or stearates (some of which are also used as mould release agents), to the curable mixtures.

The curable mixtures according to the invention can be prepared in a customary manner with the aid of known mixers (stirrers, kneaders, rolls etc.).

The curable epoxy resin mixtures according to the invention are used, in particular, in the field of surface protection, electrotechnology, lamination processes and building. They can in each case be used in a formulation which is matched to the specific application, in the unfilled or filled state, as paints, surface coatings, such as sintered powder coatings, as compression moulding compositions, dip coating resins, casting resins, injection moulding formulations, impregnation resins and adhesives, as tooling resins, lamination resins, sealants and knifing fillers, floor-covering compositions and binders for mineral aggregates.

The cured products produced using the compounds of the formula I according to the invention are distinguished by very good thermal and mechanical properties. Compared with products which have been produced without concomitant use of the orthocarbonates according to the invention, they have a comparably high heat distortion resistance with a significantly higher flexural strength and impact strength, and, in addition, the reduction in volume which is otherwise observed during curing is reduced or entirely eliminated.

The examples below illustrate the invention in greater detail.

EXAMPLE 1

Production of the reaction of 2,2-dichloro-1,3-benzodioxole with glycerol

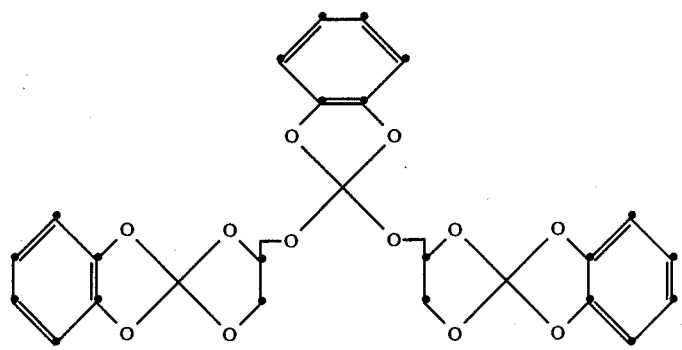

IV 30.8 g (0.335 mol) of glycerol are initially introduced in 200 ml of pyridine and 100 ml of toluene into an apparatus comprising a 500 ml three-neck flask, magnetic stirrer, thermometer, dropping funnel and drying tube. 95.5 g (0.50 mol) of 2,2-dichloro-1,3-benzodioxole are added dropwise to this mixture at 10°–20° C. with exclusion of moisture. The mixture is subsequently stirred overnight at room temperature, then poured onto ice and dilute HCl, 200 ml of toluene are added, and the organic phase is separated off and washed with 1N HCl and saturated NaHCO$_3$ solution. After drying over sodium sulfate and evaporating on a rotary evaporator, 83 g (92% of theory) of a pale yellow oil remain.

| Elemental analysis: | % of C | % of H |
|---|---|---|
| Calculated for $C_{27}H_{22}O_{12}$: | 60.11 | 3.30 |
| Found: | 60.55 | 4.29 |

The product has a molecular weight $M_n = 592$ and $M_w = 690$ determined by means of gel permeation chromatography (in THF, polystyrene as the standard).

EXAMPLE 2

Production of the reaction of 2,2-dichloro-1,3-benzodioxole with 1,1,1-trimethylolpropane

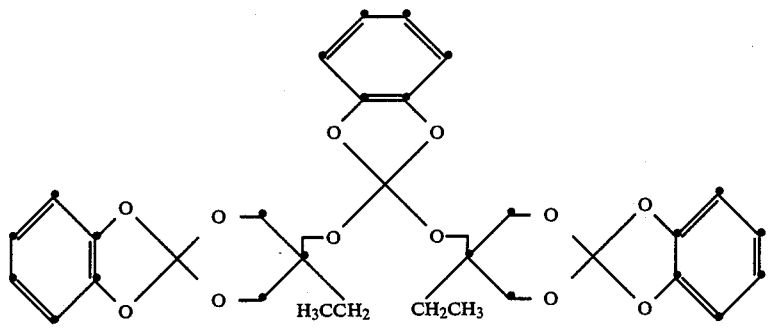

40.0 g (0.300 mol) of 1,1,1-trimethylolprpane are initially introduced in 120 ml of pyridine and 200 ml of methylene chloride into an apparatus comprising a 1000 ml three-neck round-bottom flask, magnetic stirrer, thermometer, dropping funnel and drying tube. 85.4 g (0.45 mol) of 2,2-dichloro-1,3-benzodioxole are added dropwise to this mixture at 10°-20° C. with exclusion of moisture. The mixture is subsequently stirred overnight at room temperature, then poured onto ice and dilute hydrochloric acid, and theorganic phase is separated off and washed with 1N HCl and saturated NaHCO3 solution. After drying over sodium sulfate and evaporating on a rotary evaporator, 80.8 g (87% of theory) of colourless crystals of melting point 163°-166° C. are obtained.

| Elemental analysis: | % of C | % of H |
|---|---|---|
| Calculated for $C_{33}H_{34}O_{12}$: | 63.66 | 5.50 |
| Found: | 63.62 | 5.50 |

EXAMPLE 3

Product of the reaction of 2,2-dichloro-1,3-benzodioxole with 1,2,4-butanetriol

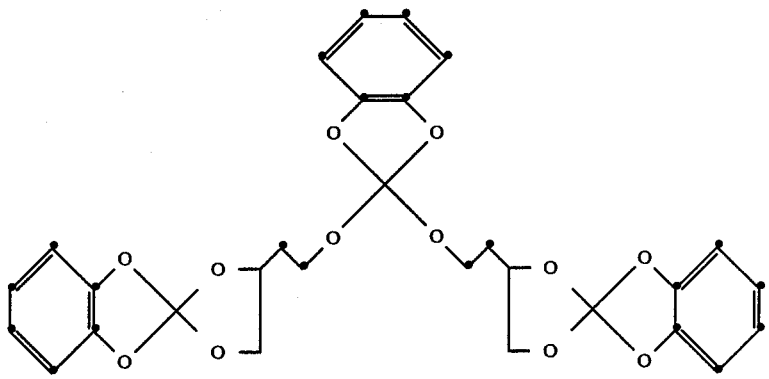

VIII 31.8 g (0.300 mol) of 1,2,4-butanetriol are initially introduced in 120 ml of pyridine and 200 ml of methylene chloride into an apparatus comprising a 500 ml three-neck round-bottom flask, magnetic stirrer, thermometer, dropping funnel and drying tube. 85.4 g (0.45 mol) of 2,2-dichloro-1,3-benzodioxole are added dropwise to this mixture at 10°-20° C. with exclusion of

VII moisture. The mixture is subsequently stirred overnight at room temperature, then poured onto ice and dilute hydrochloric acid, and the organic phase is separated off and washed with 1N HCl and saturated NaHCO3 solution. After drying over sodium sulfate and evaporating on a rotary evaporator, 86 g of a yellowish oil remain.

| Elemental analysis: | % of C | % of H |
|---|---|---|
| Calculated for $C_{29}H_{26}O_{12}$: | 61.48 | 4.63 |
| Found: | 60.55 | 4.63 |

EXAMPLE 4

Use of the product from Example 1 in a curable mixture

The curable mixtures A and B are prepared by mixing the components at room temperature, poured into moulds and subsequently cured for 4.5 hours at 100° C.

and 1 hour at 150° C. The cured mouldings have the properties shown in Table 1.

at room temperature, then poured onto ice and dilute hydrochloric acid, and the organic phase is separated off and washed with 1N HCl and saturated NaHCO$_3$ solution. After drying over sodium sulfate and evaporating on a rotary evaporator, a residue of 92.8 g of melting point 165°–168° C. (colourless powder) remains.

TABLE 1

| Mixture of substances | Tg (DSC) (°C.) | Flexural strength DIN 53452 (N/mm$^2$) | Flexural impact strength DIN 53453 (kJ/m$^2$) |
| --- | --- | --- | --- |
| A<br>100 g of a bisphenol A diglycidyl ether having an epoxide content of 5.4 eq./kg<br>13 g of m-phenylenediamine<br>0.14 g of CH$_3$CH$_2$NH$_2$.BF$_3$<br>32 g of the product from Ex. 1 | 112 | 184.0 | 13.1 |
| B<br>100 g of a bisphenol A diglycidyl ether having an epoxide content of 5.4 eq./kg<br>9.8 g of m-phenylenediamine<br>0.11 g of CH$_3$CH$_2$NH$_2$.BF$_3$ | 113 | 177.7 | 10.0 |

Table 1 shows that the cured mouldings produced using mixture of substances (A) according to the invention have better properties than mouldings produced using the same epoxy resin curing system but without an orthocarbonate of the formula I as cocomponent (B).

EXAMPLE 5

Production of the reaction of 2,2-dichloro-1,3-benzodioxole with 1,1,1-trimethylolethane

| Elemental analysis: | % of C | % of H |
| --- | --- | --- |
| Calculated for C$_{31}$H$_{30}$O$_{12}$ | 62.62 | 5.09 |
| Found: | 62.09 | 5.10 |

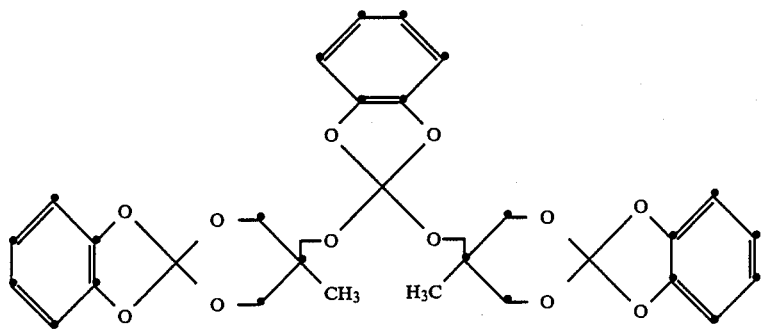

XI 39.2 g (0.33 mol) of 1,1,1-trimethylolethane are initially introduced in 160 ml of pyridine and 200 ml of methylene chloride into an apparatus comprising a 500 ml three-neck round-bottom flask, magnetic stirrer, thermometer, dropping funnel and drying tube. 93.4 g (0.50 mol) of 2,2-dichloro-1,3-benzodioxole are dropwise to this mixture at 10°–20° C. with exclusion of moisture. The mixture is subsequently stirred overnight

EXAMPLE 6

The curable mixtures of substances C and D are prepared by mixing the components (three-roll mill), poured into moulds and subsequently cured for 4.5 hours at 100° C. and for 1 hour at 150° C. The cured mouldings have the properties given in Table 2.

TABLE 2

| Mixture of substances | Tg (DSC) (°C.) | Flexural strength DIN 53452 (N/mm$^2$) | Flexural impact strength DIN 53453 (kJ/m$^2$) | Adsorption of cold water (4 days) (%) | Adsorption of boiling water (1 h) (%) |
| --- | --- | --- | --- | --- | --- |
| C<br>180 g of a bisphenol A diglycidyl ether having an epoxide content of 5.4 eq./kg,<br>2 g of CH$_3$CH$_2$NH$_2$.BF$_3$<br>20 g of the product of Example 1 | 107 | 143 | 17.3 | 0.16 | 0.32 |
| D<br>200 g of a bisphenol | | | | | |

TABLE 2-continued

| Mixture of substances | Tg (DSC) (°C.) | Flexural strength DIN 53452 (N/mm$^2$) | Flexural impact strength DIN 53453 (kJ/m$^2$) | Adsorption of cold water (4 days) (%) | Adsorption of boiling water (1 h) (%) |
| --- | --- | --- | --- | --- | --- |
| A diglycidyl ether having an epoxide content of 5.4 eq./kg 2 g of CH$_3$CH$_2$NH$_2$.BF$_3$ | 107 | 136 | 14.9 | 0.21 | 0.39 |

It can be seen from Table 2 that the cured mouldings produced using mixture of substances (C) according to the invention have better properties than mouldings produced using the same epoxy resin curing system but without an orthocarbonate of the formula I as cocomponent (D).

We claim:

1. An orthocarbonate of the formula I

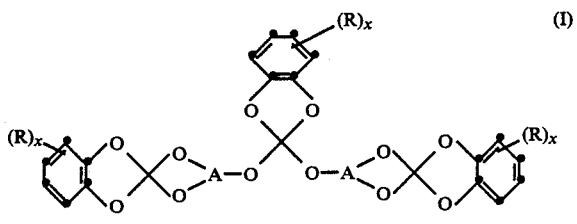

in which R is C$_1$–C$_4$alkyl, x is zero, 1 or 2, and A is a trivalent radical derived from an aliphatic triol through omission of the hydroxyl groups, the hydroxyl groups of the triol being bonded to different carbon atoms.

2. An orthocarbonate of the formula I according to claim 1, in which x is 1.

3. An orthocarbonate of formula I according to claim 1, in which x is zero.

4. An orthocarbonate of the formula I according to claim 1, in which A is derived from a 1,2,3-, 1,2,4- or a 1,3,5-triol.

5. An orthocarbonate of the formula I according to claim 1, in which A is a radical containing 3 to 24 carbon atoms.

6. An orthocarbonate of the formula I according to claim 1, in which A is a radical of the formula II $$R^1-\underset{\underset{R^1}{|}}{\overset{\overset{R^1}{|}}{C}}-\underset{\underset{R^1}{|}}{\overset{\overset{R^1}{|}}{C}}-\underset{\underset{R^1}{|}}{\overset{\overset{R^1}{|}}{C}}-R^1 \quad (II)$$

where the substituents R$^1$, independently of one another, are a C$_1$–C$_4$alkyl group or, preferably, hydrogen.

7. An orthocarbonate of the formula I according to claim 1, in which A is a radical of the formula III, IIIa or IIIb $$H_3C-CH_2-\underset{\underset{CH_2-}{|}}{\overset{\overset{CH_2-}{|}}{C}}-CH_2- \quad \underset{\underset{CH_2-}{|}}{\overset{\overset{CH_2-}{|}}{CH-}} \quad H_3C-\underset{\underset{CH_2-}{|}}{\overset{\overset{CH_2-}{|}}{C}}-CH_2-.$$
$$(III) \qquad (IIIa) \qquad (IIIb)$$

8. An orthocarbonate according to claim 1 of the formulae IV to XI

-continued

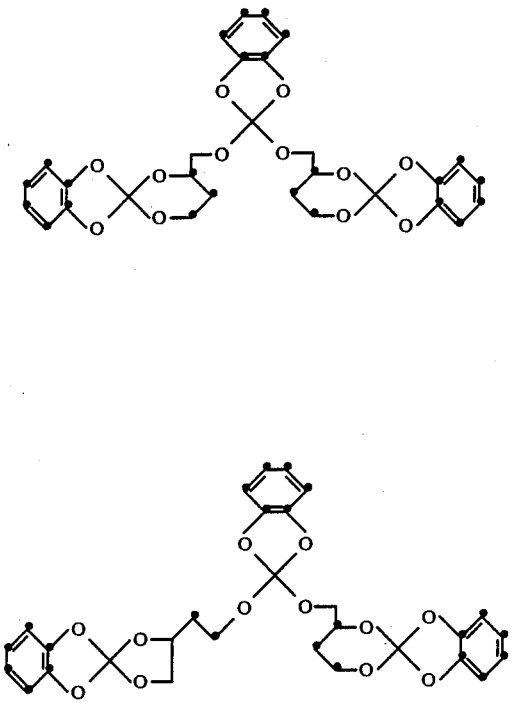
X

-continued

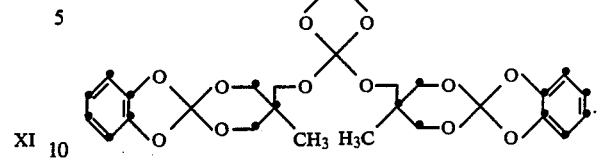
XI

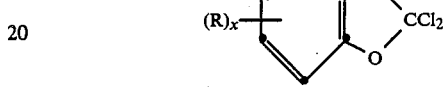
XI

9. A process for the preparation of an orthocarbonate of the formula I according to claim 1 by reacting three moles of a 2,2-dichloro-1,3-benzodioxole of the formula with two moles of a triol of the formula A(OH)$_3$ in the presence of a base, the symbols R, x and A being as defined in claim 1.

10. A curable mixture of substances containing
  (a) an orthocarbonate of the formula I according to claim 1,
  (b) an epoxy resin and
  (c) a curing agent and, if desired, a curing catalyst for the epoxy resin.

11. A mixture of substances according to claim 10, in which the amount of the orthocarbonate (a) is 5 to 50 parts by weight per 100 parts by weight of the epoxy resin (b).

12. An orthocarbonate of the formula I according to claim 1, prepared by reacting 3 moles of 2,2-dichloro-1,3-benzodioxole with 2 moles of glycerol.

* * * * *